US008962853B2

(12) United States Patent
Cheung et al.

(10) Patent No.: US 8,962,853 B2
(45) Date of Patent: Feb. 24, 2015

(54) CHEMICAL PROBE COMPOUNDS THAT BECOME FLUORESCENT UPON REDUCTION, AND METHODS FOR THEIR USE

(71) Applicant: Life Technologies Corporation, Carlsbad, CA (US)

(72) Inventors: Ching-Ying Cheung, San Ramon, CA (US); Diane Gray, Eugene, OR (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/975,675

(22) Filed: Aug. 26, 2013

(65) Prior Publication Data

US 2014/0127679 A1    May 8, 2014

Related U.S. Application Data

(63) Continuation of application No. 12/908,152, filed on Oct. 20, 2010, now Pat. No. 8,546,580, which is a continuation of application No. 11/870,238, filed on Oct. 10, 2007, now abandoned, which is a continuation of application No. 11/366,784, filed on Mar. 1, 2006, now abandoned.

(60) Provisional application No. 60/657,944, filed on Mar. 1, 2005.

(51) Int. Cl.
*C07D 291/00* (2006.01)
*C07C 211/00* (2006.01)
*G01N 33/58* (2006.01)
*C07D 211/62* (2006.01)
*C07D 295/112* (2006.01)
*C07D 417/06* (2006.01)
*C07D 417/14* (2006.01)
*C09B 23/04* (2006.01)
*C12Q 1/04* (2006.01)
*C12Q 1/18* (2006.01)
*G01N 33/52* (2006.01)

(52) U.S. Cl.
CPC ............ *G01N 33/582* (2013.01); *C07D 211/62* (2013.01); *C07D 295/112* (2013.01); *C07D 417/06* (2013.01); *C07D 417/14* (2013.01); *C09B 23/04* (2013.01); *C12Q 1/04* (2013.01); *C12Q 1/18* (2013.01); *G01N 33/52* (2013.01)
USPC ............................ 548/122; 546/134; 564/428

(58) Field of Classification Search
USPC ............................ 548/122; 546/134; 564/428
See application file for complete search history.

(56) References Cited

U.S. PATENT DOCUMENTS

| 4,558,130 | A | 12/1985 | Buckler et al. |
|---|---|---|---|
| 4,656,141 | A | 4/1987 | Birks et al. |
| 5,445,944 | A | 8/1995 | Ullman |
| 5,658,751 | A | 8/1997 | Yue et al. |
| 5,795,729 | A | 8/1998 | Lee |
| 5,863,753 | A | 1/1999 | Haugland et al. |
| 5,912,139 | A | 6/1999 | Iwata et al. |
| 6,057,120 | A | 5/2000 | Heindl et al. |
| 6,468,753 | B1 | 10/2002 | Smith et al. |
| 7,378,255 | B2 * | 5/2008 | Horn et al. ..................... 435/25 |
| 2002/0010279 | A1 | 1/2002 | Satcher et al. |
| 2004/0110308 | A1 | 6/2004 | Laikhter et al. |
| 2004/0234945 | A1 | 11/2004 | Horn et al. |
| 2006/0199242 | A1 | 9/2006 | Cheung et al. |
| 2008/0254501 | A1 | 10/2008 | Cheung et al. |
| 2011/0117591 | A1 | 5/2011 | Cheung et al. |

FOREIGN PATENT DOCUMENTS

| EP | 0190740 | B1 | 8/1986 |
|---|---|---|---|
| EP | 0431456 | B1 | 11/1990 |
| EP | 0441222 | A3 | 8/1991 |
| EP | 0620283 | A1 | 3/1994 |
| EP | 0574769 | B1 | 4/1996 |
| EP | 0831327 | B1 | 9/1997 |
| EP | 1853598 | | 11/2012 |
| JP | 63277680 | | 11/1988 |
| JP | 2003277385 | | 10/2003 |
| WO | WO-91/09139 | | 6/1991 |
| WO | WO-93/06487 | | 4/1993 |
| WO | WO-2006/094104 | | 9/2006 |

OTHER PUBLICATIONS

067366575, , "Extended European Search Report mailed Jul. 14, 2010".

Borchardt, R. T. et al., "Stereopopulation Control.III. Facilitation of Intramolecular Conjugate Addition of the Carboxyl Group", Journal of the American Chemical Society, 94:26, Dec. 27, 1972, 9175-9182.

(Continued)

*Primary Examiner* — Nizal Chandrakumar

(74) *Attorney, Agent, or Firm* — Life Technologies Corporation

(57) ABSTRACT

Chemical stain compounds containing a fluorophore and a reducible quenching unit are disclosed. The reducible quenching unit quenches the fluorophore while in its oxidized state. Upon reduction, the quenching properties of the quenching unit are diminished or eliminated. The chemical compounds can be used in a variety of applications, including the detection of bacterial cells, monitoring the electron transport chain function of bacterial cells, monitoring the oxidation state of non-biological systems, and assaying the effectiveness of antibacterial or antimicrobial agents.

1 Claim, 13 Drawing Sheets

(56) References Cited

OTHER PUBLICATIONS

Haugland, Richard P., "Molecular Probes Handbook of Fluorescent Probes and Research Chemicals", *10.5: Substrates for Miscellaneous Enzymes*, Sixth Edition, Molecular Probes, Inc., 1996, 236-237.

Haugland, Richard P., "Molecular Probes Handbook of Fluorescent Probes and Research Products", Sixth Edition, 1996, 13-15.

Johansson, M. K. et al., "Intramolecular Dimers: Anew Design Strategy for Fluorescence-Quenched Probes", *Chem.Eur.J.*, vol. 9,, 2003, 3467-3471.

Josephine, et al., "Syntheses of covalently-linked porphyrin-quinone complexes", *Journal of Heterocyclic Chemistry* Wiley-Blackwell Publishing, Inc, US LNKD, vol. 17, No. 4,, Jun. 1, 1978, 737-744.

Kong, et al., "Syntheses of covalently-linked porphyrin-quinone complexes.", *J. Heterocycl. Chem.*, 17, 1978, 737.

Lakowicz, J. R., "Energy Transfer", *Principles of Fluorescence Spectroscopy*, 2nd Ed. Plenum Publishing Corp., New York, NY, 1999, 367-394.

Lozinsky, E. et al., "Dual fluorophore-nitroxide Molecules: Models for study of intramolecular Fluorescence Quenching and novel Redox Probes an Spin Traps", *Recent Res. Devel. Photochem. & Photobiol* vol. 5, 2001, 41-55.

Magnera, et al., "Triple-quadrupole secondary ion mass spectrometry of low-temperature solids: collision-activated dissociation of large cluster ions", *J. Am. Chem. Soc.*, 106, 1984, 5040.

Ryabov, A. D. et al., "Spectrophotometric Kinetic Study and Analytical Implications of the Glucose Oxidase-Catalyzed Reduction of [MIII (LL)2Cl2]+ Complexes by D-Glocuse (M=Os and Ru, LL=2,2'-Bipyridine and 1, 10-Phenanthroline Type Ligands)", JBIC, 4, 1999, 175-182.

Song, Aimin et al., "Photophysical Properties of Polyads Containing a Fluorescein Moiety", *Dyes and Pigments*, vol. 42, 1999, 149-158.

Wasielewski, M. et al., "Photoinduced electron Transfer in meso-Triphenyl triptycenylporphyr in-Quinones", *J. Am. Chem. Soc.*, vol. 106, 1984, 5043-5045.

Woltman, S. J. et al., "Chromatographic Detection Using Tris (2,2'-Bipyridl)Ruthenium (III) as a Fluorogenic Electron-Transfer Reagent", *Anal. Chem.*, vol. 71, 1999, 1504-1512.

Zhang, Hong et al., "Photoinduced Intramolecular Electron Transfer in an Anthraquinone-Fluorscein-Carbazole Model", *Journal of Photochemistry and Photobiology A: Chemistry*, vol. 103, 1997, 63-67.

\* cited by examiner

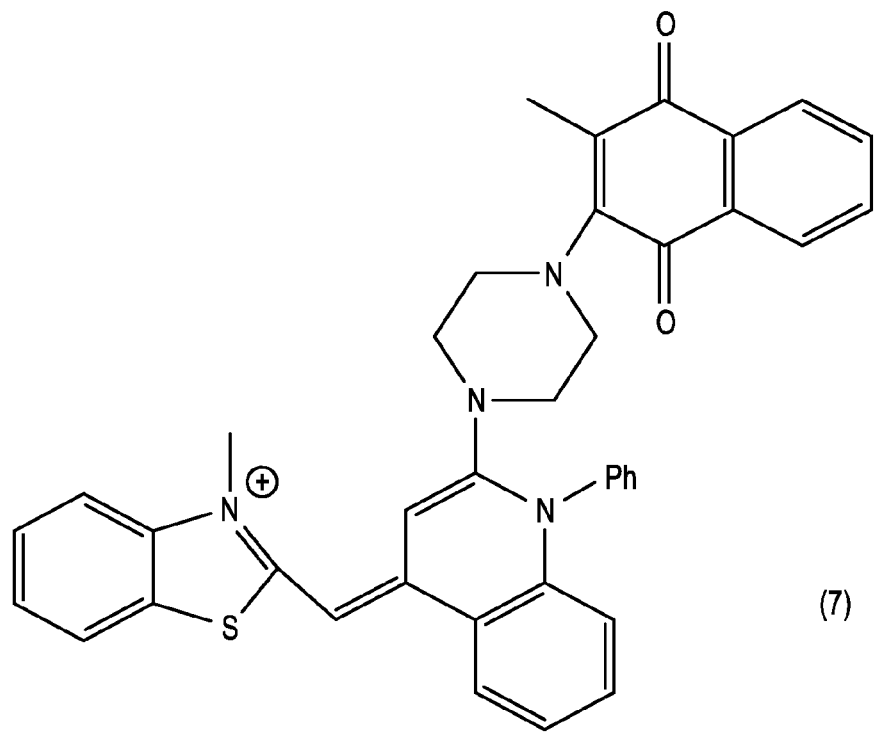
*FIG. 1G* (7)
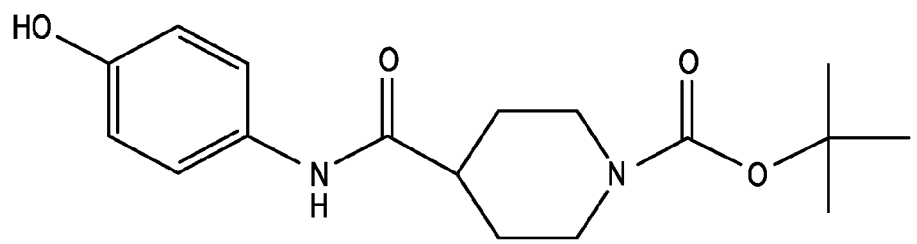
*FIG. 1H* (8)
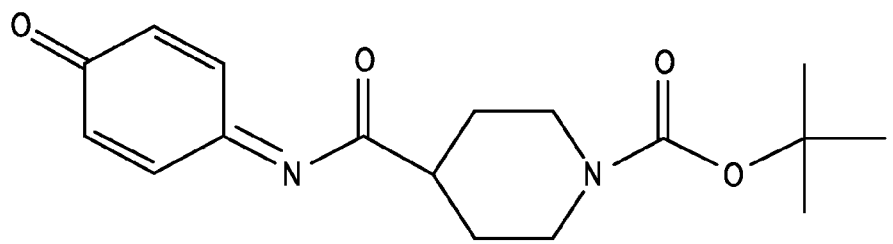
*FIG. 1I* (9)

CHEMICAL PROBE COMPOUNDS THAT BECOME FLUORESCENT UPON REDUCTION, AND METHODS FOR THEIR USE

CROSS REFERENCE TO RELATED APPLICATIONS

This application is a continuation of U.S. patent application Ser. No. 12/908,152, filed Oct. 20, 2010, which is a continuation of U.S. patent application Ser. No. 11/870,238 (abandoned), filed Oct. 10, 2007, which is a continuation of U.S. patent application Ser. No. 11/366,784 (abandoned), filed Mar. 1, 2006, which claims priority to U.S. Provisional Patent Application Ser. No. 60/657,944 filed Mar. 1, 2005, the contents of which are incorporated herein by reference.

FIELD OF THE INVENTION

The invention relates to quenched chemical stain compounds that can be reduced to a fluorescing form, and methods for their use.

DESCRIPTION OF RELATED ART

Oxidation and reduction are natural metabolic functions of living cells. Methods and materials for the detection of the oxidative states of cells have been desirable for some time, as they allow researchers to achieve a better understanding of the conditions within cells or cell compartments. Various methods have been used to date.

One approach is to use a chemical probe that is not fluorescent outside of the cell, but which becomes oxidized to a fluorescent derivative once it enters the cell. Dihydrorhodamine and dihydroethidium are examples of such chemicals that oxidize inside a cell compartment (Haugland, Richard P.; Handbook of Fluorescent Probes and Research Products; ninth edition; 2002). These stains are used to gain entry into live cells, and are not used for measuring redox functions in cells. The stains can be readily oxidized by molecular oxygen.

Derivatives of quinones, naphthaquinones, and anthraquinones have been reported to quench fluorescence when linked to a fluorophore (Kong, J. C. Y. and Loach, R. A.; J Heterocycl. Chem. 17: 737 (1978); Wasielewski, M. R. and Nienczyk, M. P.; J. Am. Chem. Soc. 106: 5040 (1984)).

Israel Patent Application No. 156355 (filed Jun. 9, 2003; published Jan. 4, 2004) suggests the preparation of compounds containing a reversible quinone/hydroquinone redox site, a spacer, and a fluorophore. The compounds do not fluoresce when in the oxidized state, but become fluorescent once reduced. The compounds are suggested as being useful as fluorescent redox probes for chemical, biochemical, and biophysical investigations.

U.S. Pat. No. 6,057,120 (issued May 2, 2000) describes the use of redox-active compounds for the determination of an analyte. The redox pairs have a benzoquinoxaline substructure. The compounds are suggested to be used to determine the reducing or oxidizing activities of cells and enzymes.

5-Cyano-2,3-ditolyl tetrazolium chloride ("CTC"; commercially available from Polysciences, Inc.; Warrington, Pa.) is a monotetrazolium redox dye which produces a fluorescent formazan ("CTF") upon reduction. According to the manufacturer, the dye can be used in flow cytometry with excitation using a 488 nm laser and detection in the red color region (Data Sheet #486; September 1999).

Various species can effect the oxidation of dyes, complicating the interpretation of experimental results. Examples of such species include molecular oxygen, superoxide, and hydrogen peroxide. This oxidation is used in connection with compounds such as dihydrorhodamine and dihydroethidium, where the neutral reduced form can enter cells by diffusion, and be subsequently oxidized to the fluorescent dye. These materials are not generally used to measure the oxidative function of cells, as atmospheric oxygen can oxidize them as well.

Despite advances made to date, there still exists a need for chemical probes and methods for the monitoring indicators of metabolic functions within cells, tissues, and other materials.

SUMMARY OF THE INVENTION

Chemical compound probes containing a fluorophore unit and a reducible quenching unit are disclosed. The probes can also contain a linker unit covalently bonded to the fluorophore unit and the reducible quenching unit. Upon reduction, the reducible quenching unit exhibits a diminished quenching ability, and fluorescence of the compound can be detected. The probes can be used in a variety of applications to monitor the conditions of cells (including bacteria), tissues, and other materials. Applications include monitoring of change in oxidation state of a material, change in electron transport chain function, and change in cellular vitality after treatment with antibiotics, inhibitors, or other chemical compounds.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W and 1X show chemical intermediates and compounds that are illustrative of embodiments of the invention.

DETAILED DESCRIPTION OF THE INVENTION

Figure 1A:
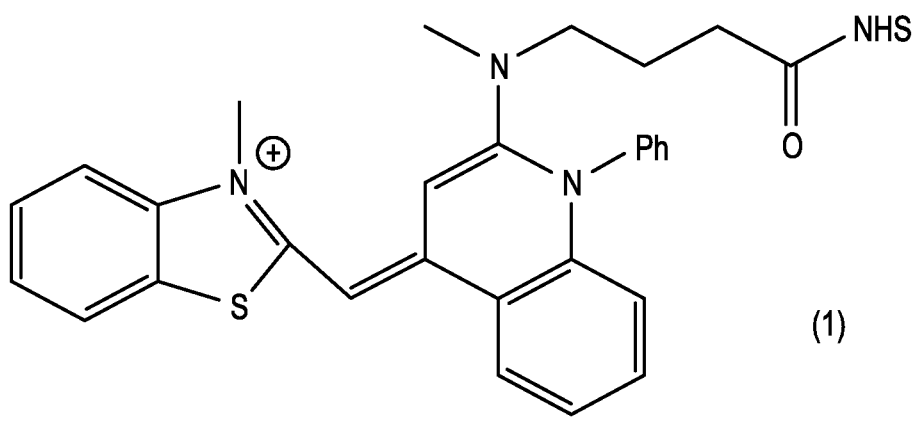
Figure 1B:
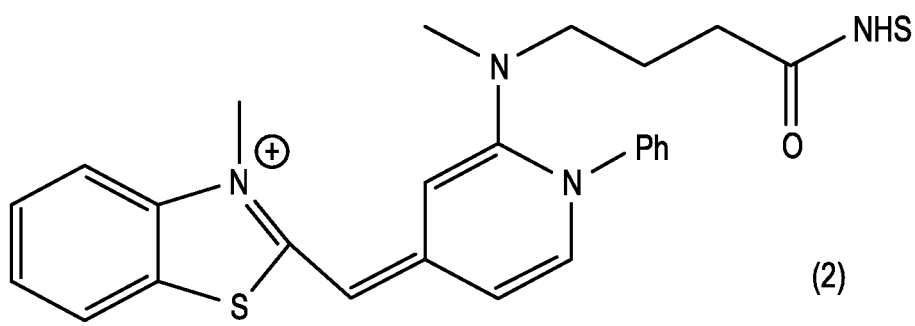
Figure 1C:
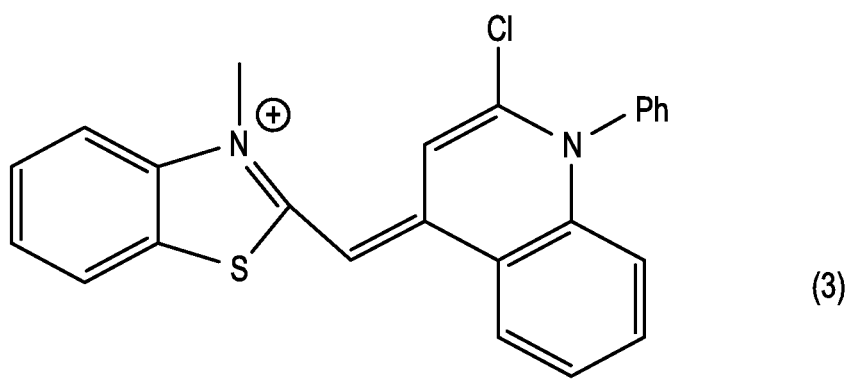
Figure 1E:
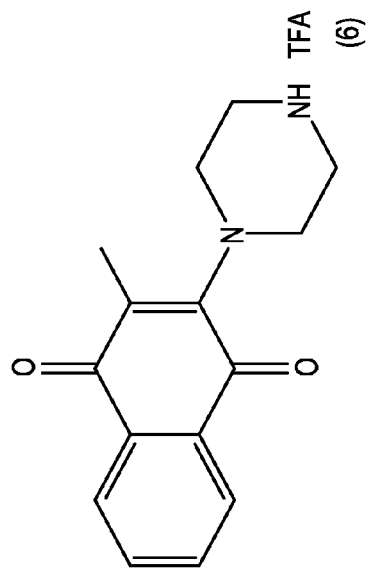
Figure 1D:
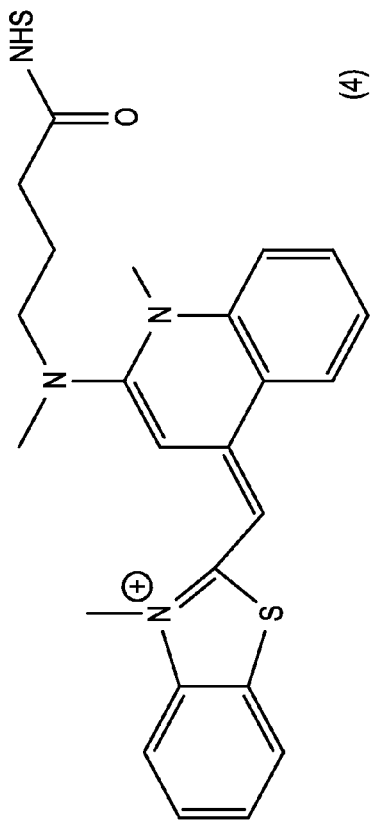

While compositions and methods are described in terms of "comprising" various components or steps (interpreted as meaning "including, but not limited to"), the compositions and methods can also "consist essentially of" or "consist of"

the various components and steps, such terminology should be interpreted as defining essentially closed-member groups.

Compounds

One embodiment of the invention is directed towards chemical compound probes. The chemical compound probe comprises a fluorophore unit ("probe"), and a reducible quenching unit. The fluorophore unit and the reducible quenching unit can be covalently linked or non-covalently linked. The covalent linkage can be direct with no intervening linker unit, or can be indirect by use of a linker unit. Non-covalent linkage can be through formation of a coordination complex, an ionic bond, a pi-pi interaction, van der waals interaction, or other linkage methods that bring the fluorophore unit and the reducible quenching unit into a position whereby the reducible quenching unit can partially or fully quench the fluorophore unit. Where the chemical compound probe is charged (either positively or negatively), the embodiment of the invention also includes salts containing one or more counterions. Examples of positively charged counterions include alkali metal ions, alkaline earth metal ions, transition metal ions, ammonium, substituted ammonium ions, sodium, potassium, lithium, calcium, magnesium, and ammonium counterions. Examples of negatively charged counterions include halides (chloride, bromide, iodide), acetate, sulfate, alkanesulfonate, arylsulfonate, phosphate, perchlorate, tetrafluoroborate, tetraarylboride, nitrate, anions of aromatic carboxylic acids, and anions of aliphatic carboxylic acids.

The chemical compound probes have the advantageous property of not being fluorescent in the absence of DNA. Once in contact with DNA, the probes become fluorescent (i.e., they are stains and not dyes). This property provides for low matrix backgrounds outside of cells.

Generally, the chemical compound probes can comprise one of the following two structures, where FU is the fluorophore unit, L is a linker unit, and RQU is the reducible quenching unit.

FU-RQU; or

FU-L-RQU

The reducible quenching unit when in its oxidized state partially or fully quenches the fluorescence of the fluorophore unit in the probe. This quenching is preferably at least about 50%, at least about 60%, at least about 70%, at least about 80%, at least about 90%, at least about 95%, at least about 96%, at least about 97%, at least about 98%, at least about 99%, and ideally about 100%. Higher values are more preferred. This reduction in fluorescence can be measured relative to the fluorescence of the probe when the reducible quenching unit has been reduced to a reduced quenching unit (its non-reduced quenching form). The quenching percentage can be calculated as: ((unquenched fluorescence minus quenched fluorescence) divided by unquenched fluorescence) times 100%. The FU, RQU, and optionally the L are preferably covalently bonded to each other.

The fluorophore unit can generally comprise any quenchable fluorophore unit. Examples of such fluorophore units include fluorescein, BODIPY (4,4-difluoro-4-bora-3a,4a-diaza-s-indacene; boron dipyromethene difluoride), rhodamines, cyanines, and coumarins.

The reducible quenching unit can generally comprise any unit that can quench the fluorophore unit when in its oxidized, non-reduced state, and that partially or fully loses its quenching ability upon being reduced to its reduced state. Examples of such reducible quenching units include quinone, naphthaquinone, anthraquinone, quinonemethine, copper (Cu(II) to Cu(I)), sulfate ($SO_4^{2-}$ to $SO_3^-$), and nitrate ($NO_3^-$ to $NO_2^-$). Presently preferred reducible quenching units include quinone, naphthaquinone, and anthraquinone.

The linker unit can generally be any linker unit that places the fluorophore unit and the reducible quenching unit in a suitable spatial and electronic configuration whereby the reducible quenching unit can partially or fully quench the fluorophore unit. The linker unit can be a linear linker, a branched linker, a cyclic linker, an aromatic linker, a polycyclic aromatic linker, an unsaturated linker (e.g. containing double and/or triple bonds), or other linkers. The linker can also contain two or more different types of linker portions, such as an unsaturated portion and a cyclic portion. The linker can comprise one or more different types of atoms. For example, the linker can comprise carbon atoms, hydrogen, oxygen, sulfur, chlorine, fluorine, iodine, phosphorous, silicon, nitrogen, other atoms, or combinations thereof. Examples of such linker units include polyethylene glycol, $PO_3$ (FU-O—P(=O)—O-RQU), SO (FU-S(=O)—RQU), and $SO_2$ (FU-S(=O)$_2$-RQU).

Figure 1F:
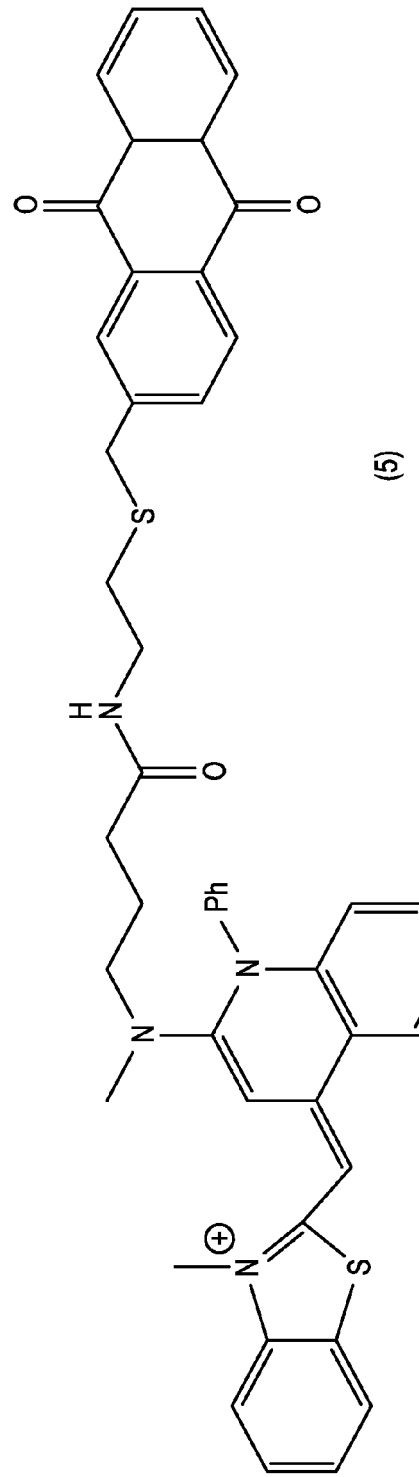
Figure 1J:
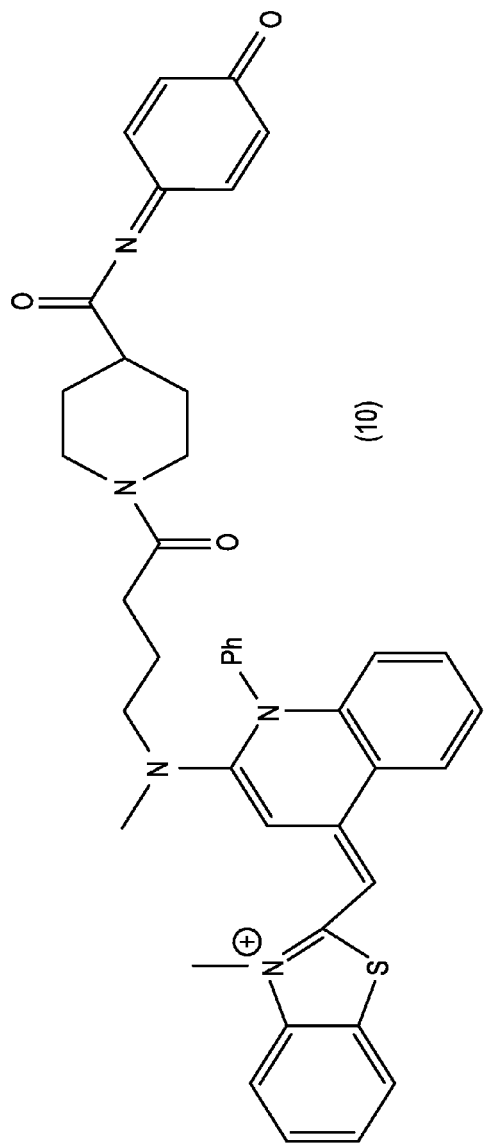
Figure 1K:
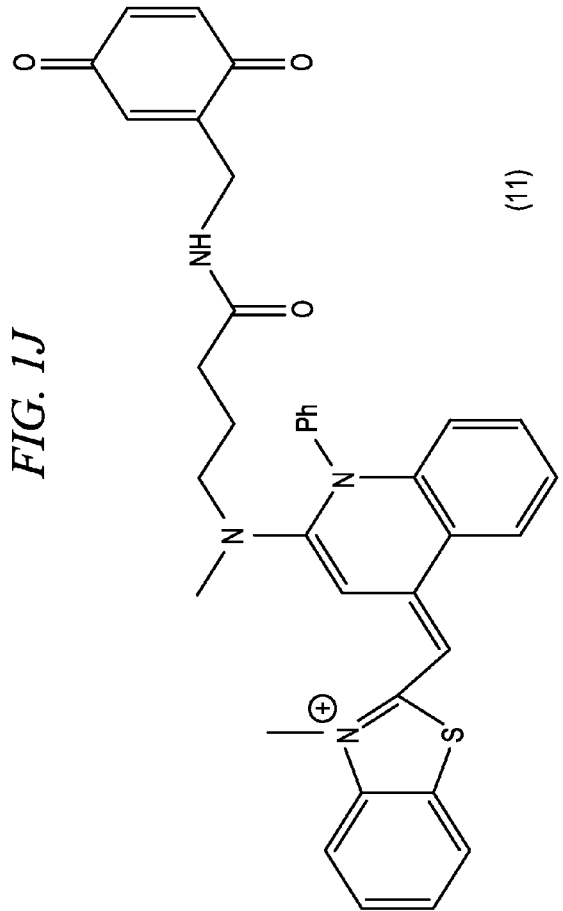
Figure 1L:
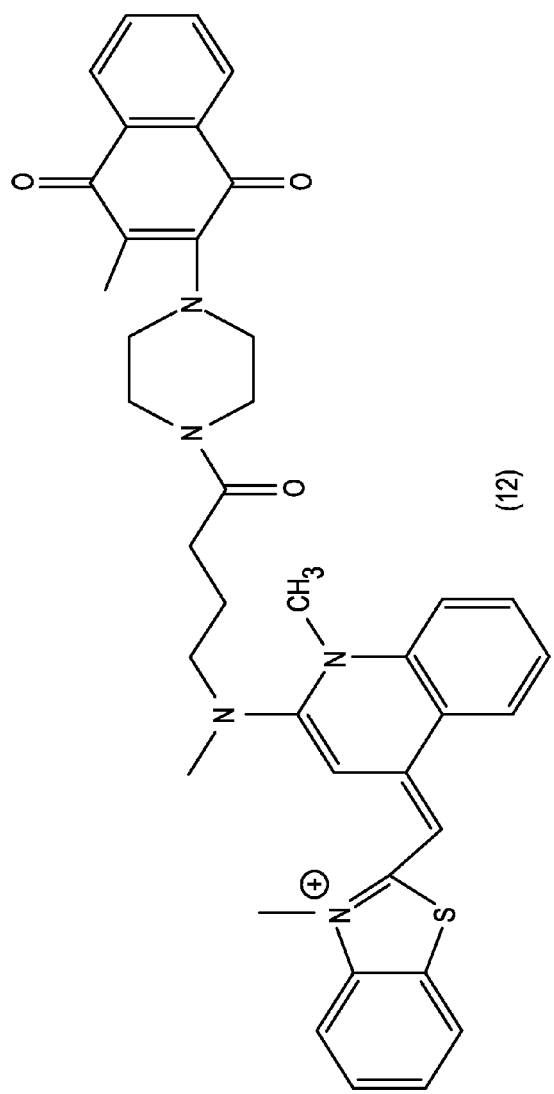
Figure 1N:
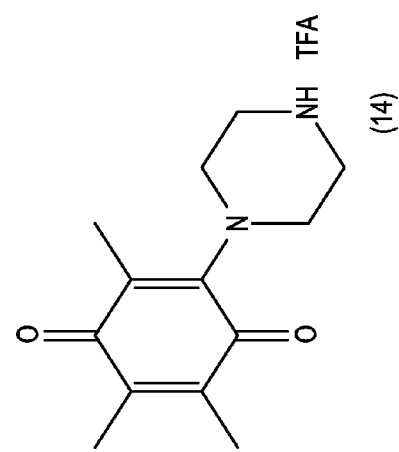
Figure 1M:
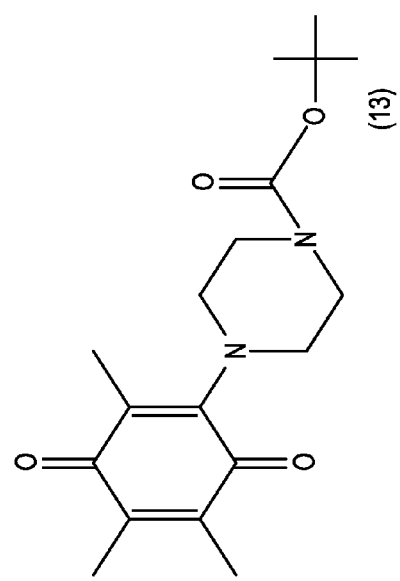
Figure 1P:
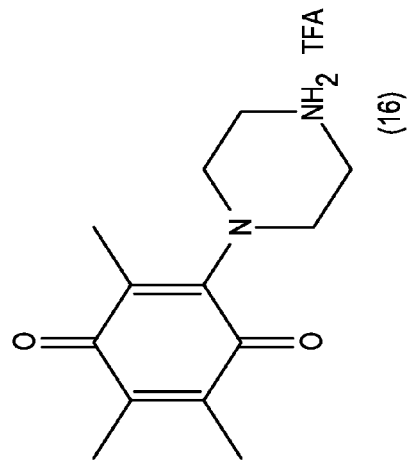
Figure 1O:
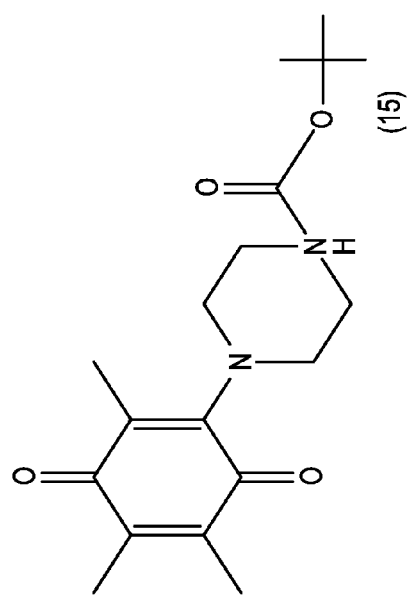
Figure 1Q:
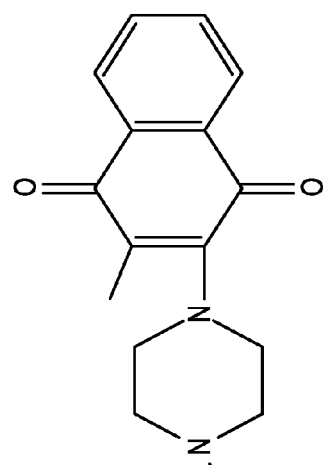
Figure 1Q:
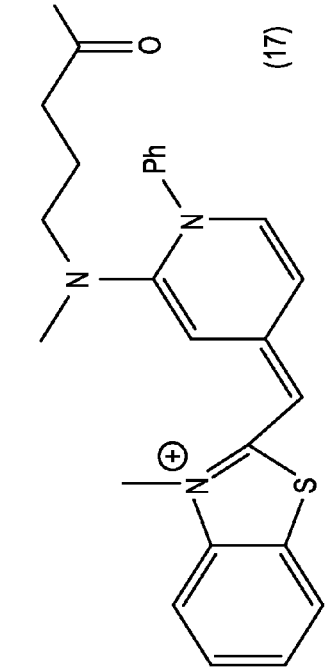
Figure 1R:
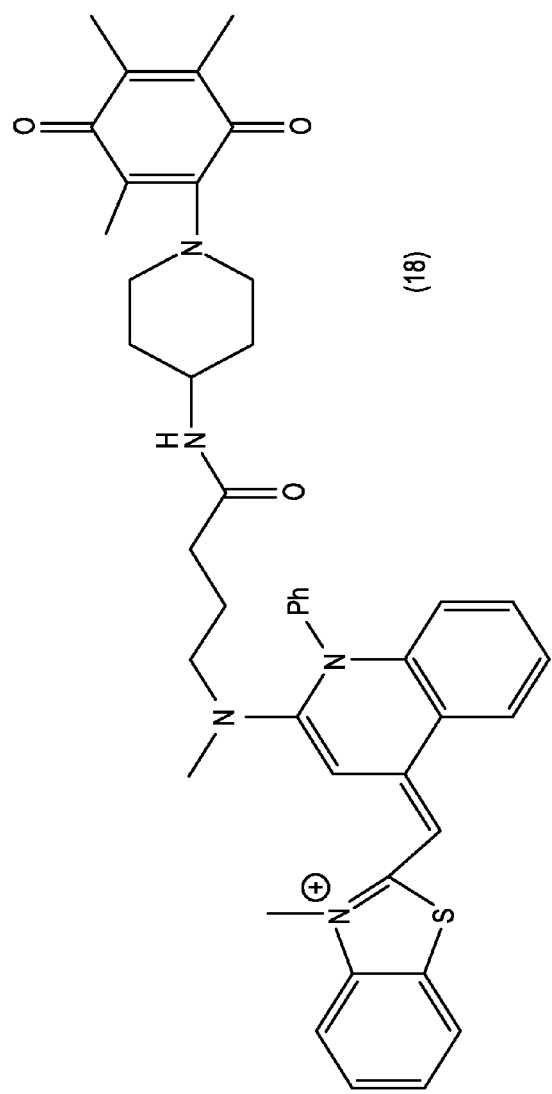
Figure 1S:
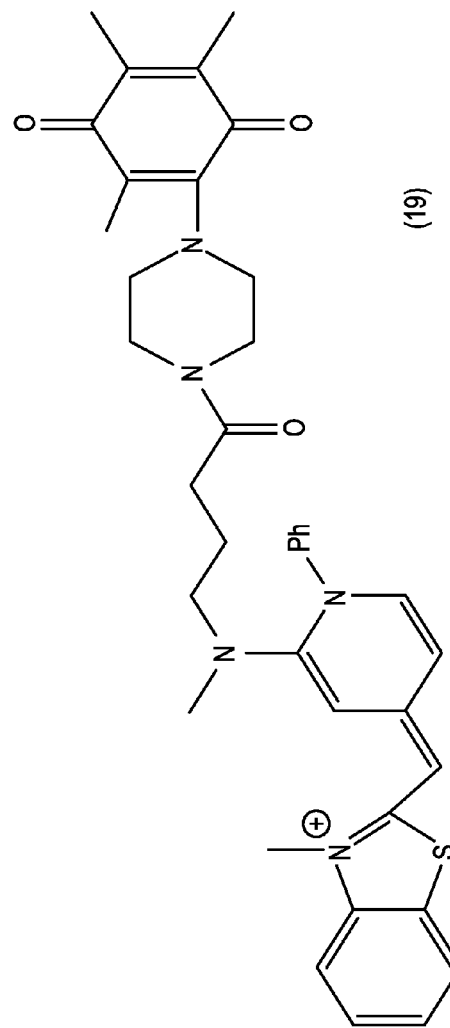
Figure 1T:
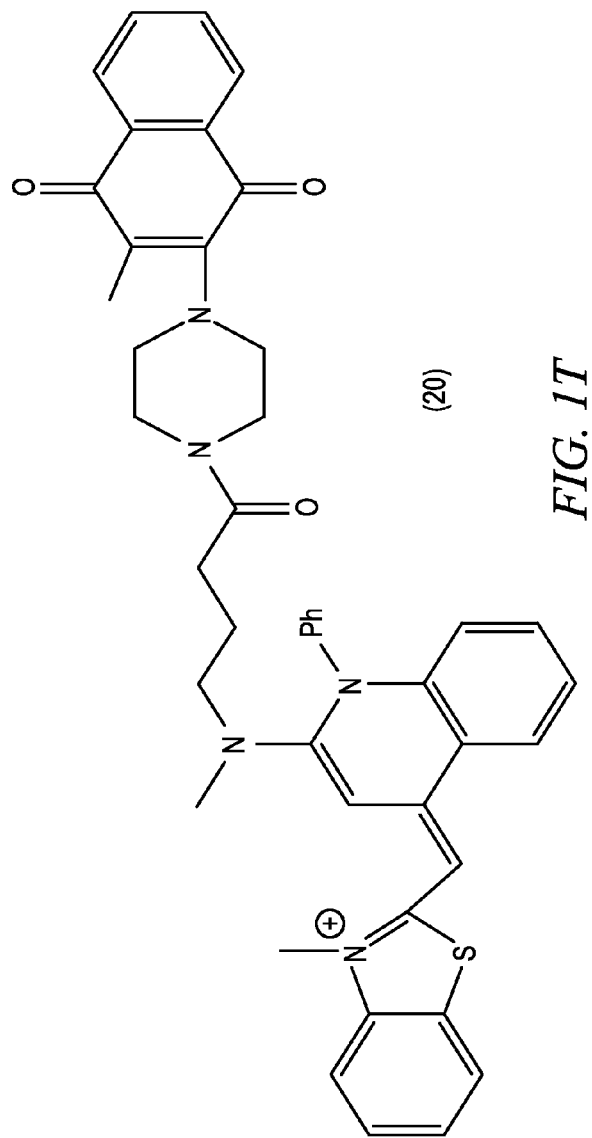
Figure 1U:
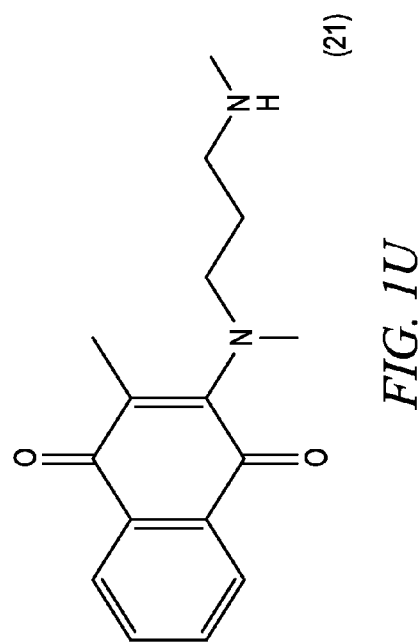
Figure 1V:
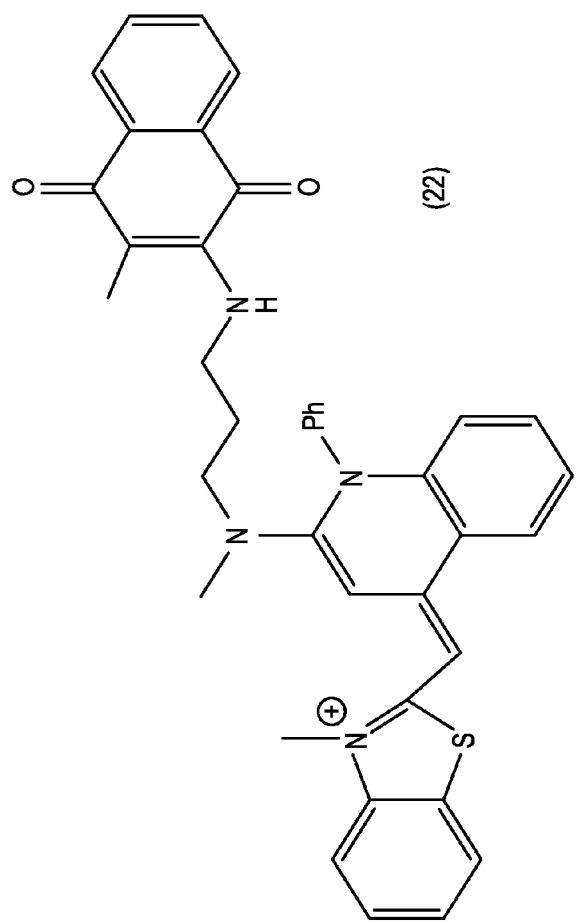
Figure 1W:
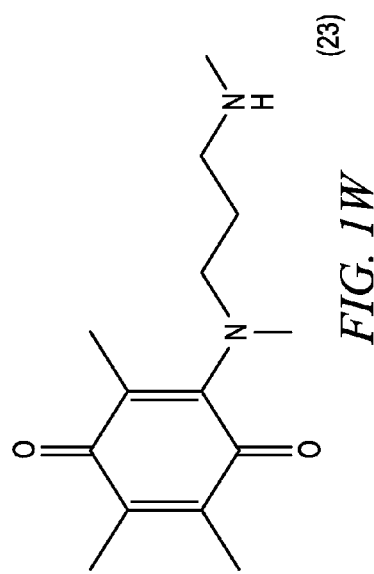
Figure 1X:
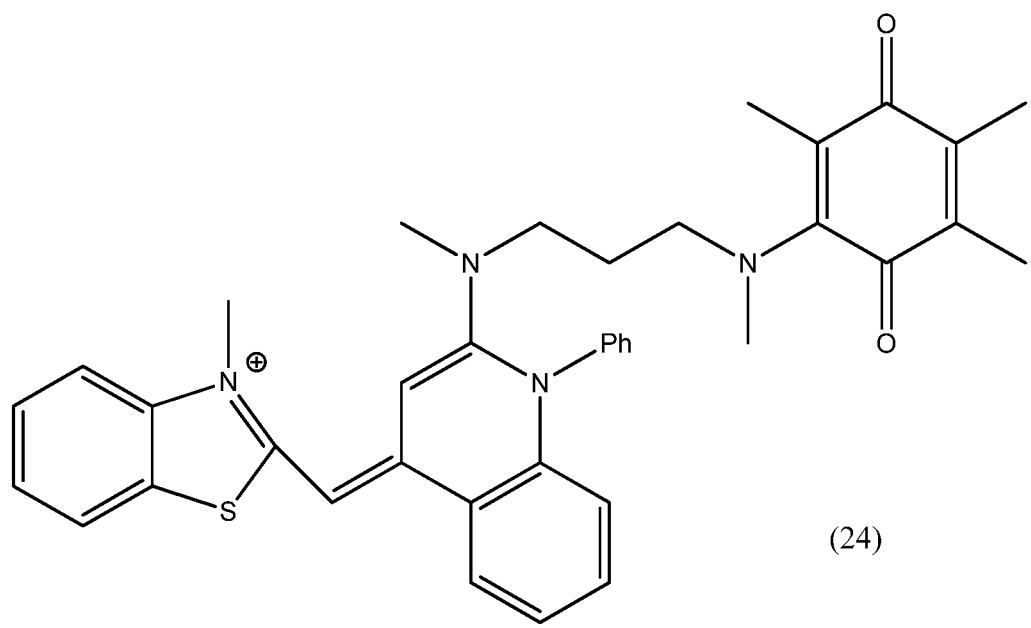

Specific chemical compound probes include: compound (5) shown in FIG. 1F, compound (10) shown in FIG. 1J, compound (11) shown in FIG. 1K, compound (18) shown in FIG. 1R, compound (19) shown in FIG. 1S, compound (22) shown in FIG. 1V, and compound (24) shown in FIG. 1X.

Kits

An additional embodiment of the invention is directed towards kits containing one or more of the above described chemical compound probes. The kit can comprise a first container comprising one or more of the above described chemical compound probes. The first container can further comprise a solvent. The solvent can generally be any solvent, and can include aqueous, non-aqueous, or mixed solvents (e.g. water and DMSO). Examples of solvents are water, DMSO, ethanol, methanol, dimethylacetamide, dimethylformamide (DMF), and N-methylpyrrolidinone (NMP). The solvent can further comprise a buffer. The kit can further comprise instruction protocols. The kit can further comprise a positive control sample. The kit can further comprise a negative control sample. The kit can further comprise a second container or multiple additional containers for processing samples.

The one or more chemical compound probes can be present in the first container at a "working" concentration, or as a concentrated stock solution that requires dilution prior to use. The kit can further comprise a second container comprising a solvent or buffer solution useful for diluting the stock solution.

Methods of Preparation

An additional embodiment of the invention is directed towards methods for the preparation of the above described chemical compound probes. The chemical compound probes can generally be prepared by the synthetic methods described in the Examples.

Methods of Use

An additional embodiment of the invention is directed towards methods for the use of the above described chemical compound probes to assay, detect, or monitor the oxidative or reductive environment of a cell, tissue, or other material. One probe can be used individually, or multiple probes can be used in combination. The probes can be used with biological samples (e.g., cells, bacterial cells, tissues, organisms), or with non-biological samples (e.g., electrolytic cells, water samples).

The methods can comprise providing a material to be assayed, contacting the material with one or more of the above described chemical compounds to form a test sample, and determining the fluorescence of the test sample. The fluorescence can be determined by irradiating the test sample with light or energy of a suitable wavelength to excite the chemical compound. Light sources include LED and laser light sources, such as a 488 nm argon ion laser. The degree of fluorescence (or lack thereof) can be correlated with the oxidative or reductive environment of the material. For example, in an oxidative environment, the reducible quenching unit would be in its oxidative state, quenching the fluorophore unit, thereby resulting in little or no fluorescence. In a reducing environment, the reducible quenching unit would be in its reduced state, not quenching the fluorophore unit, thereby resulting in fluorescence. By varying the oxidative or reductive environment of the material, the degree of detected fluorescence would change.

The above described chemical compound probes can be used in a variety of applications, both in vivo and in vitro. The probes can be used in generally any condition to detect and/or monitor the oxidative or reductive environment. DNA can be added to the environment to enhance the response of the probe.

For example, the probe can be contacted with a target such as a cell (including bacteria), a collection of cells, a tissue, or an organism under conditions suitable for uptake of the probe into the target. If the target has an environment suitable for reduction of the reducible quenching unit, then the probe can be detected by its fluorescence properties. The fluorescence of the probe can be detected at a single point in time, or can be monitored over multiple points or continuously. The detection can be performed using instrumentation such as flow cytometry, fluorometers, epifluorescence microscopes, microplate readers, and fluorescence readers.

The uptake can be through diffusion or active uptake by the target. Alternatively, various chemical or mechanical treatments may be performed to facilitate uptake. Example treatments include addition of surfactants, performing electroporation, microinjection, or addition of peptide or other membrane disruption agents. Agents such as EDTA or detergents such as Pluronic® F127 (Pluronic is a registered trademark of BASF Corporation; Mount Olive, N.J.) can be used to assist dye entry into Gram-negative bacteria. Agents such as Tween® 20 (Tween is a registered trademark of ICI Americas, Inc.; Bridgewater, N.J.) can be used to assist dye entry into both Gram-negative and Gram-positive bacteria.

Cells can be generally any type of cell. For example, the cells can be Gram-positive bacterial cells, Gram-negative bacterial cells, fungal cells, insect cells, fish cells, amphibian cells, bird cells, reptile cells, or mammalian cells. Bacterial cells are presently preferred due to their lack of a nucleus. The target can be a single cell, or a population of cells. The population of cells can be the same, or a mixture of different cells. The intensity of the resulting fluorescence of the chemical compound probes is generally greater in healthy bacterial cells, and lower (or not changed) in weakened or dead bacterial cells.

An additional embodiment of the invention is directed towards methods of evaluating the efficacy of antibacterial (antibiotic) compounds. A sample of bacteria can be treated with one or more of the above described chemical compound probes, and the fluorescence can be measured (the initial fluorescence). The same or similar sample of bacteria can be treated with a prospective antibacterial or antibiotic compound. The antibacterial/antibiotic treated sample is subsequently contacted with the same one or more chemical compound probes, and the fluorescence is again measured (the final fluorescence). The two fluorescence values can be compared, and the difference in fluorescence can be determined (e.g. final fluorescence minus initial fluorescence). The magnitude of this difference can be correlated with the efficacy of the antibacterial or antibiotic treatment. For example, a small difference in fluorescence would suggest that the antibacterial or antibiotic treatment was ineffective. Conversely, a large difference in fluorescence would suggest that the antibacterial or antibiotic treatment was effective. This large difference would suggest that the antibacterial or antibiotic treatment had a substantial effect on the vitality of the bacteria. Typically, an effective treatment would be indicated by a reduced increase in fluorescence relative to a control.

An additional embodiment of the invention is directed towards methods of assaying the electron transport system of a target, and of identifying inhibitors. A target can be treated with a chemical or other agent suspected of being capable of inhibiting the target's electron transport system. The treated sample can be contacted with one or more of the above described chemical compound probes, and the fluorescence can be measured. The treated sample can comprise DNA. This fluorescence value can be compared with a control sample that was not treated with the suspected inhibitor, but contacted with the chemical compound probe. Alternatively, the target can be contacted with the chemical compound probe prior to contacting with the suspected inhibitor. The two fluorescence values can be compared, and the difference in fluorescence can be determined (e.g. final fluorescence minus initial fluorescence, or final fluorescence minus control fluorescence). The magnitude of this difference can be correlated with the efficacy of the suspected inhibitor. For example, a small difference in fluorescence would suggest that the suspected inhibitor was ineffective at inhibiting the electron transport system of the target. Conversely, a large difference in fluorescence would suggest that the suspected inhibitor was effective at inhibiting the electron transport system of the target. This large difference would suggest that the suspected inhibitor had a substantial effect on the vitality of the target. Typically, an effective inhibitor would be indicated by a higher initial fluorescence and a lower final fluorescence.

An additional embodiment of the invention is directed towards methods of monitoring change in the oxidation state of a non-biological system. DNA can be added to the environment to enhance the response of the probe. The system can be a fluid, a gel, a liquid, a chemical reactor, an environmental sample, or so on. The system can be contacted with one or more of the above described chemical compound probes, and the fluorescence can be measured at a first time point to provide a first fluorescence. A second fluorescence can be measured after a particular time period has elapsed, or after subjecting the system to some change or chemical treatment. The fluorescence can be measured at discrete times, or can be measured continuously. Additional subsequent fluorescence values such as a third fluorescence value, fourth fluorescence value, fifth fluorescence value, sixth fluorescence value, and so on can be determined. The second or subsequent fluorescence values can be compared against the first fluorescence value to monitor change in the oxidation state of the non-biological system. An increase in the fluorescence indicates that the system is becoming less oxidizing, and more reducing. A decrease in the fluorescence indicates that the system is becoming more oxidizing, and less reducing. The two or more fluorescence values can be plotted in a graph, prepared as a list or table of results, or displayed in other conventional manners.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation of Compound (5)

A mixture of 40 mg compound (1), 60 mg 2-(2-aminoethylthio)methylanthraquinone, and 45 microliters triethylamine was stirred in 1 mL dimethylformamide overnight at room temperature. Product compound (5) was purified by column chromatography on silica gel with 4:4:3:1 ethyl acetate:chloroform:methanol:acetic acid.

Example 2

Preparation of Compound (6)

A mixture of 4.4 g of 2-methyl-1,4-napthoquinone and 11.9 g of 1-tBoc-piperazine was heated in 90 mL of a methanol/dichloromethane (1:1, v/v) solvent mixture at about 45° C. for 24 hours. The solvent was evaporated and the crude product was purified on a silica gel column to yield 1.08 g of desired intermediate. Trifluoroacetic acid (1 mL) was added to 100 mg of this tBoc-protected piperazine in 5 mL of dichloromethane, and after one hour at room temperature, all of the volatile components were removed and the product compound (6) was used "as is" without further purification.

Example 3

Preparation of Compound (7)

Triethylamine (0.21 mL) was added to a mixture of 70 mg of compound (3) and 0.28 mmole of compound (6) in 5 mL of dichloroethane, and the resulting reaction mixture was heated at 55-60° C. for one hour. The reaction was cooled to room temperature and volatile components were evaporated. The crude product compound (7) was purified using silica gel column chromatography with 2:2:1 ethyl acetate:chloroform:methanol.

Example 4

Preparation of Compound (8)

A mixture of 1.63 g of the N-hydroxysuccinimidyl ester of 1-tBoc-4-piperidinecarboxylic acid, 0.82 g of 4-aminophenol, and 1.4 mL of triethylamine in 10 ml of dichloromethane was refluxed for 16 hours. The crude product compound (8) was purified using silica gel column chromatography with ethyl acetate:hexane.

Example 5

Preparation of Compound (9)

Lead tetraacetate (0.41 g) was added to 0.27 g of compound (8) in 2 mL of acetic acid. The resulting mixture was stirred at room temperature for one hour. About 50 mL of ethyl acetate was added, followed by 30 mL of water. The organic layer was separated and dried over anhydrous magnesium sulfate. The crude was purified using silica gel column chromatography with ethyl acetate:hexane to obtain 24 mg of compound (9).

Example 6

Preparation of Compound (10)

A solution of 15 mg of compound (9) was dissolved in 1 mL of dichloromethane, and 0.5 mL of trifluoroacetic was added. After stifling at room temperature for 10 minutes, all of the volatile components were removed under reduced pressure, and the residue was dissolved in 5 mL of dichloromethane. To this deprotected intermediate, a solution of 25 mg of compound (1) in 2.5 mL of DMF was added, followed by 28 uL of triethylamine. The resulting mixture was stirred at room temperature for several hours. All volatile components were evaporated, and the product compound (10) was purified using silica gel column chromatography with ethyl acetate:chloroform:methanol.

Example 7

Preparation of Compound (11)

A sample of 3.12 g of 2-cyano-1,4-dimethoxybenzene was reduced by 1 g of lithium aluminum hydride in 20 mL of THF at 0° C. to yield 3 g of 2-aminomethyl-1,4-dimethoxybenzene. This was then refluxed in a 1:1 (v/v) mixture of acetic acid and 48% aqueous hydrobromic acid overnight. The volatile components were removed under reduced pressure, and the crude 2-aminomethyl-1,4-hydroquinone HBr salt was used "as is" without further purification. Triethylamine (0.4 mL) was added to a mixture of 50 mg of compound (1) and 0.6 mmole of 2-aminomethyl-1,4-dihydroquinone HBr salt in 2 mL of dichloroethane, and stirred overnight. The crude dihydroquinone was then oxidized to the desired quinone compound (11) with ceric ammonium nitrate in a water/acetonitrile mixture.

Example 8

Preparation of Compound (12)

Compound (6) (0.3 mmole) was added to a mixture of about 0.2 mmole compound (4) in 2 mL of dichloroethane at room temperature. Next, about 1 mmole of triethylamine was added. The crude product compound (12) was purified using silica gel column chromatography with 5:5:2 ethyl acetate:chloroform:methanol.

Example 9

Preparation of Compound (13)

A mixture of 2 g of 2,3,5-trimethylquinone and 3.7 g of 1-tBoc-piperazine was heated at 50° C. in 30 mL of a 1:1 (v/v) dichloromethane: methanol mixture overnight. An additional portion of 3.7 g of 1-tBoc-piperazine was added and heated for an additional 3 days. Volatile components were evaporated under reduced pressure, and the crude product was purified using silica gel column chromatography with 10:9:1 hexane:chloroform:acetic acid to yield 0.775 of compound (13).

Example 10

Preparation of Compound (14)

Trifluoroacetic acid (2 mL) was added to 0.775 g of compound (13) in 5 mL of dichloromethane at room temperature. The mixture was stirred for 2 hours. All volatile components were evaporated, and the product compound (14) was used without further purification.

Example 11

Preparation of Compound (15)

A mixture of 1 g of 2,3,5-trimethylquinone and 1.6 g of tBoc-4-aminopiperidine was heated in 20 mL of a 1:1 (v/v) dichloromethane: methanol mixture overnight. An additional 0.5 g of the tBoc-4-aminopiperidine was added and heated for an additional 3 days. Volatile components were evaporated under reduced pressure, and the crude product was purified using silica gel column chromatography with 10:9:1 hexane:chloroform:acetic acid to yield 0.16 g of compound (15).

Example 12

Preparation of Compound (16)

Trifluoroacetic acid (1 mL) was added to 0.16 g of compound (15) in 2 mL of dichloromethane. The mixture was stirred for 4 hours. All volatile components were evaporated, and the product compound (16) was used without further purification.

Example 13

Preparation of Compound (17)

A mixture of 24 mg of compound (4), 0.064 mmole of compound (6), and 0.04 mL of triethylamine was stirred in 2 mL of dichloroethane at room temperature for 2 hours. At the end of the period, volatile components were evaporated, and the crude product compound (17) was purified using silica gel column chromatography with 2:2:1 ethyl acetate:chloroform:methanol.

Example 14

Preparation of Compound (18)

A mixture of 0.24 mmole of compound (1), 0.48 mmole of compound (16), and 0.1 mL of triethylamine in 1 mL of dichloroethane was stirred at room temperature for several hours. The reaction was diluted with chloroform and washed with water, brine, and dried over magnesium sulfate. The crude compound (18) thus obtained was further purified using silica gel column chromatography with 2:2:1 ethyl acetate:chloroform:methanol.

Example 15

Preparation of Compound (19)

A mixture of 0.039 mmole of compound (2), 0.078 mmole of compound (14), and 0.1 mL of triethylamine was stirred in 2 mL of dichloromethane at room temperature for several hours. The reaction was diluted with chloroform and washed with water, brine, and dried over magnesium sulfate. The crude compound (19) thus obtained was further purified using silica gel column chromatography with 5:5:2 ethyl acetate:chloroform:methanol.

Example 16

Preparation of Compound (20)

Triethylamine (0.1 mL) was added to 0.12 mmole of compound (6) and 50 mg of compound (1) in 2 mL of dichloromethane. The mixture was stirred at room temperature for 4 hours. The reaction was diluted with chloroform and washed with water, brine, and dried over magnesium sulfate. The crude compound (20) thus obtained was further purified using silica gel column chromatography with 2:2:1 ethyl acetate:chloroform:methanol to yield 28 mg of compound (20).

Example 17

Preparation of Compound (21)

To 0.13 g of 2-methyl-1,4-naphthoquinone in 20 mL of a 1:1 (v/v) methanol:dichloromethane mixture, 0.75 mL of N,N'-dimethylpropanediamine is added and heated at 50° C. overnight. The volatile components are removed under reduced pressure and the crude is purified using silica gel column chromatography with 4:1 chloroform:methanol to yield 60 mg of compound (21).

Example 18

Preparation of Compound (22)

A mixture of 22 mg of compound (3), 15.4 mg of compound (21), and 0.02 mL of triethylamine was stirred in 2 mL of dichloroethane at 60° C. for several hours. The reaction mixture was diluted with chloroform, washed with water, brine, and dried over magnesium sulfate. The crude compound (22) was purified using silica gel column chromatography with ethyl acetate:chloroform:methanol.

Example 19

Preparation of Compound (23)

A mixture of 0.95 g of 2,3,5-trimethylquinone and 6.65 mL of N,N'-dimethylpropanediamine in a 1:1 (v/v) methanol:dichloromethane mixture was heated at 50° C. overnight. Volatile components were evaporated under reduced pressure, and the crude compound (23) was purified using silica gel column chromatography with 4:1 chloroform:methanol.

Example 20

Preparation of Compound (24)

A mixture of 0.115 mmole compound (3), 0.173 mmole of compound (23), and 50 uL of triethylamine in 5 mL of dichloroethane was heated at 60° C. for 3 hours. The reaction was diluted with chloroform and washed with water, brine, and dried over magnesium sulfate. The crude compound (24) was purified using silica gel column chromatography with ethyl acetate:chloroform:methanol.

Example 21

Titration Studies

Figure 2:
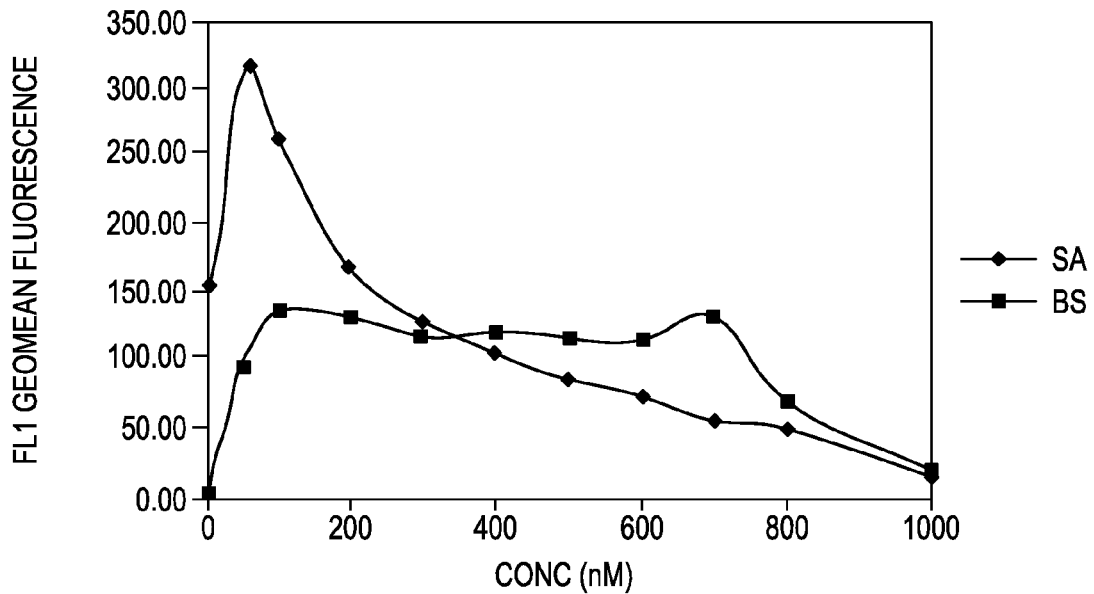
FIG. 2 shows a titration curve for Gram-positive Staphylococcus aureus (S. aureus) and Bacillus subtilis (B. subtilis). The x-axis represents the concentration of compound (18) in nM, while the y-axis represents FL1 GeoMean fluorescence.
Figure 3:
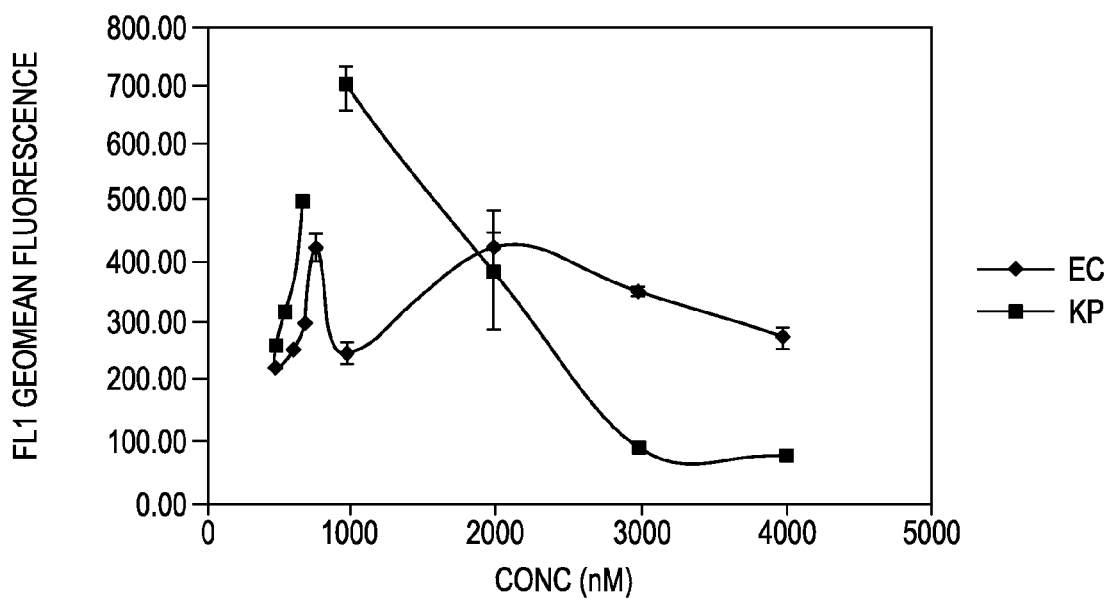
FIG. 3 shows a titration curve for Gram-negative Escherichia coli (E. coli) and Klebsiella pneumoniae (K. pneumoniae). The x-axis represents the concentration of compound (18) in nM, while the y-axis represents FL1 GeoMean fluorescence.

A titration series was performed on cultured bacteria. Chemical compound (18) was used at concentrations ranging from 10 nM to 1 uM for *S. aureus* and *B. subtilis* (FIG. 2), and 500 nM to 4 uM for *E. coli* and *K. pneumoniae* (FIG. 3). Low nanomolar concentrations were found to work well for *S. aureus* (50-100 nM), about 500 nM is about optimal for *B. subtilis*, and about 1 uM are preferred for the Gram-negative organisms tested.

Example 22

Staining of Gram-Positive and Gram-Negative Microorganisms

Gram-positive and Gram-negative bacteria were labeled using compound (18). *S. aureus* and *B. subtilis* were used as examples of Gram-positive bacteria, and *E. coli* and *K. pneumoniae* were used as examples of Gram-negative bacteria. Cells were diluted in buffer to about $10^6$ cells/mL. The bacteria were contacted with compound 18 (500 nM) for 10 minutes in Hank's Balanced Salt Solution (HBSS) or various other buffers such as PBS. The samples were analyzed by flow cytometry using a Becton Dickinson FACScan™ instrument (Becton, Dickinson and Company; Franklin Lakes, N.J.) containing a 488 nm argon ion laser. Cells were analyzed directly without washing, or optionally, were fixed with 1-4% formaldehyde prior to flow cytometric analysis.

TABLE 1

Staining of *S. aureus*

| Buffer | FL1 GeoMean fluorescence |
| --- | --- |
| Unlabeled | 1.02 |
| Sodium chloride | 2171.61 |
| Sodium chloride + 10 mM glucose | 2183.44 |
| PBS | 1976.41 |
| PBS + 1 mM EDTA | 1583.19 |
| PBS + 0.01% Tween-20 | 2909.97 |
| PBS + 0.1% Pluronic | 1685.21 |
| HBSS | 2168.52 |

TABLE 2

Staining of *B. subtilis*

| Buffer | FL1 GeoMean fluorescence |
| --- | --- |
| Unlabeled | 4.92 |
| Sodium chloride | 951.93 |
| Sodium chloride + 10 mM glucose | 943.79 |
| PBS | 902.15 |
| PBS + 1 mM EDTA | 57.75 |
| PBS + 0.01% Tween-20 | 844.66 |
| PBS + 0.1% Pluronic | 470.35 |
| HBSS | 902.22 |

TABLE 3

Staining of *E. coli*

| Buffer | FL1 GeoMean fluorescence |
| --- | --- |
| Unlabeled | 1.07 |
| Sodium chloride | 12.43 |
| Sodium chloride + 10 mM glucose | 11.52 |
| PBS | 30.25 |
| PBS + 1 mM EDTA | 70.92 |
| PBS + 0.01% Tween-20 | 44.48 |
| PBS + 0.1% Pluronic | 136.43 |
| HBSS | 42.1 |

TABLE 4

Staining of *K. pneumoniae*

| Buffer | FL1 GeoMean fluorescence |
| --- | --- |
| Unlabeled | 1 |
| Sodium chloride | 9.16 |
| Sodium chloride + 10 mM glucose | 9.7 |
| PBS | 17.91 |
| PBS + 1 mM EDTA | 48.67 |
| PBS + 0.01% Tween-20 | 29 |
| PBS + 0.1% Pluronic | 78.1 |
| HBSS | 19.9 |

These results confirm that compounds prepared according to aspects of the instant invention are effective at interacting with, and detecting both Gram-positive and Gram-negative bacterial cells. The results also show that the buffer can be chosen to modulate the observed fluorescence, due to enhancing uptake of the stain compound into the cells or a capability of the buffer to maintain the cell vitality.

Example 23

Time Course Treatments

*S. aureus* were treated with various antibiotics: penicillin/streptomycin (100 U/mL), azide (10 mM), CCCP (carbonyl cyanide m-chlorophenylhydrazone; 10 uM), or antimycin A (20 uM), and incubated in growth medium. Control samples that were untreated were also prepared.

Figure 4:
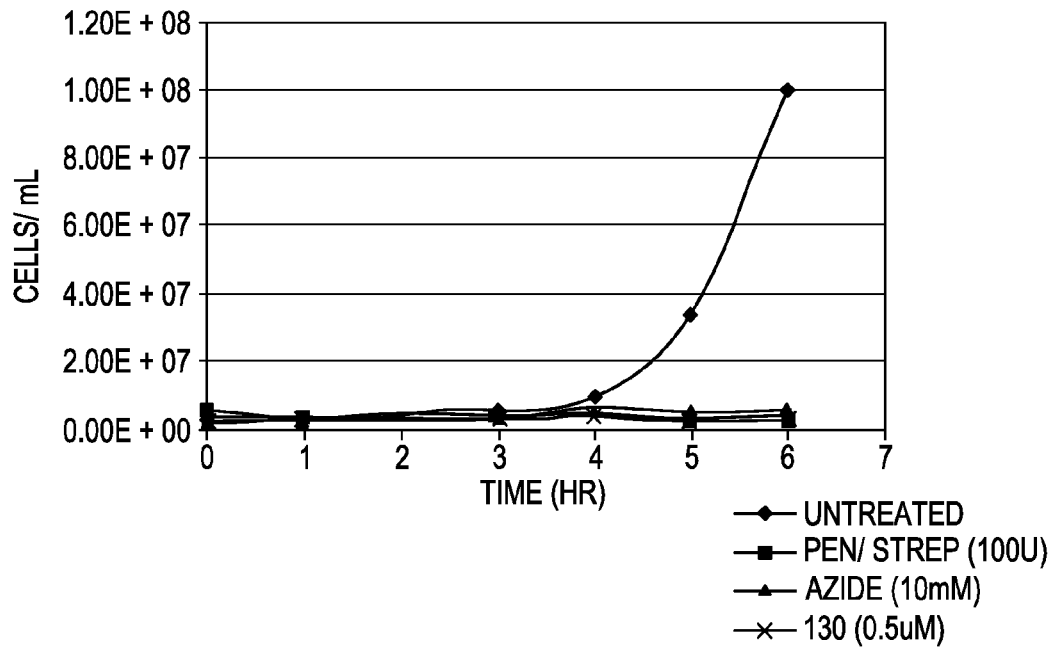
FIG. 4 shows growth curve data obtained during a time-course experiment. The x-axis represents time in hours, while the y-axis represents S. aureus cells per mL.
Figure 5:
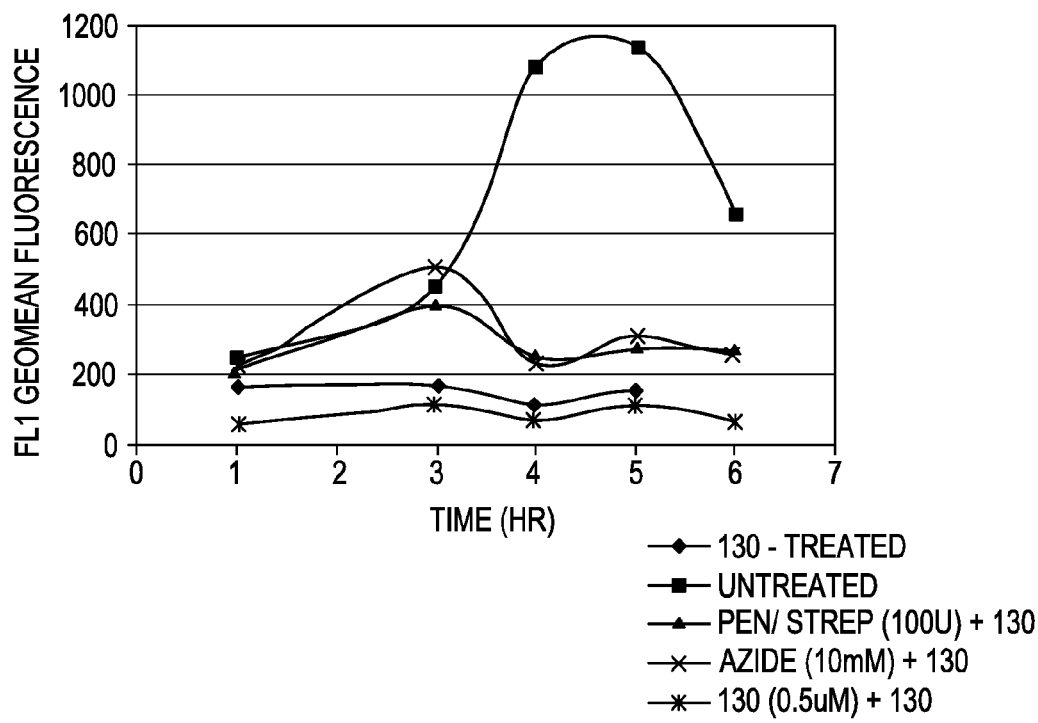
FIG. 5 shows fluorescence data obtained during a time-course experiment. The x-axis represents time in hours, while the y-axis represents FL1 GeoMean fluorescence.

Samples were taken once every hour for six hours and stained with 500 nM compound (18) for 10 minutes, then analyzed by flow cytometry using a Becton Dickinson FACSCalibur™ instrument (Becton, Dickinson and Company; Franklin Lakes, N.J.) containing a 488 nm argon ion laser. Not only did the treated cells not proliferate, but the signal from the stain in treated samples decreased once the cells entered 'log-growth' phase as compared to the untreated control. FIG. 4 shows the growth curve data, while FIG. 5 shows the fluorescence signal data. This experiment also demonstrated that compound (18), when present in broth culture medium, prevented proliferation of *S. aureus*.

Example 24

Stability of Fluorescence

Figure 6:
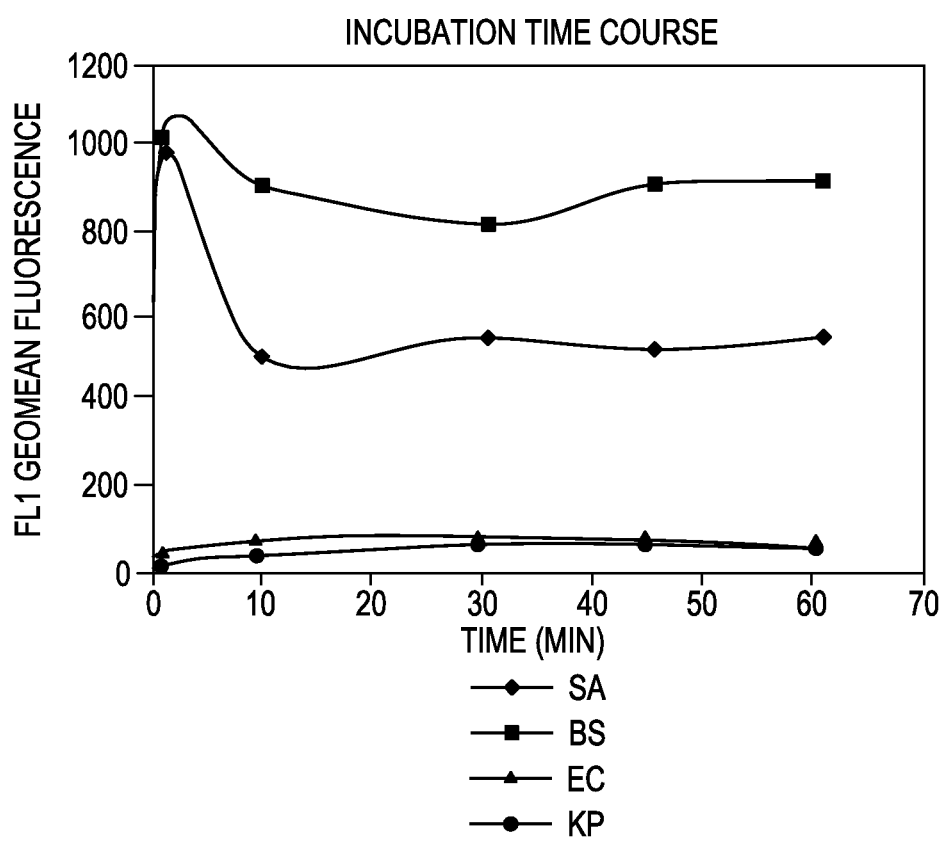
FIG. 6 shows fluorescence data obtained during a time-course experiment. The x-axis represents time in hours, while the y-axis represents FL1 GeoMean fluorescence.

Compound (18) was contacted with cultures of *S. aureus*, *B. subtilis*, *E. coli*, and *K. pneumoniae*. The fluorescence of the samples were monitored for one hour. The signal developed very quickly for *S. aureus* and *B. subtilis*, and stabilized within 10 minutes. The signal was stable for at least one hour (FIG. 6).

Example 25

Compatibility with Fixed Samples

A culture of *S. aureus* was grown to log-phase, and washed and diluted in HBSS to $10^6$ cells per mL. Samples of 1 mL each were aliquotted to six flow cytometry tubes. CCCP was added to three of the samples at a final concentration of 10 µM. The samples were incubated for 1-5 minutes. Compound (18) was added at a final concentration of 100 nM, and the samples were allowed to sit for 10 minutes. The +/− CCCP tubes were divided into two sets: one set received 1 mL of 100% ethanol, and the other set received 100 .mu.L of 10% formaldehyde (methanol-free). The samples were analyzed using a Becton Dickinson FACSCalibur as described in Example 23. The results are shown in the following table.

TABLE 5

Fixation assays with compound (18)

| CCCP | Fixation agent | Fluorescence |
|---|---|---|
| No | None | 1720 |
| Yes | None | 110 |
| No | Ethanol | 135 |
| Yes | Ethanol | 53 |
| No | Formaldehyde | 936 |
| Yes | Formaldehyde | 274 |

These results indicate that fixing samples with 1% formaldehyde maintains the fluorescence signal better than fixing with 50% ethanol.

Example 26

Electron Transport System Inhibition Assay Using Compound (18)

*S. aureus* and *E. coli* were treated with known inhibitors of the electron transport system (ETS) to determine if reductase moieties in the ETS would reduce exemplary stain compounds. The ETS inhibitors included rotenone (1 mM), antimycin A (20 uM), azide (10 mM), and CCCP (10 uM). The bacteria were diluted in PBS buffer and treated with the various ETS inhibitors, stained with 500 nM stain compound (18) for 10 minutes, and then analyzed by flow cytometry using a Becton Dickinson FACSCalibur™ instrument (Becton, Dickinson and Company; Franklin Lakes, N.J.) containing a 488 nm argon ion laser.

TABLE 6

ETS assays with compound (18)

| Inhibitor | S. aureus | E. coli |
|---|---|---|
| Untreated | 351.91 | 85.33 |
| Rotenone | 32.75 | 24.05 |
| Antimycin A | 59.41 | 34.65 |
| Azide | 801.54 | 15.27 |
| CCCP | 4.19 | 150.7 |

For *S. aureus*, the fluorescence signal obtained from the treated samples were lower than that for the untreated sample, except for samples treated with azide. For *E. coli*, the fluorescence signal obtained from the treated samples were lower than that for the untreated sample, except for samples treated with CCCP. Treatment with rotenone or antimycin A demonstrated reduced fluorescence values with both organisms. Reduced fluorescence values are indicative of less cellular reductase activity. These results show that the stain compound (18) can be used to monitor the vitality of cells treated with various drugs and inhibitors.

Example 27

Electron Transport System Inhibition Using Compound (19)

Stain compound (19) was assayed according to the procedure outlined in Example 23.

TABLE 7

ETS assays with compound (19)

| Inhibitor | S. aureus | E. coli |
|---|---|---|
| Untreated | 248.1 | 59.78 |
| Rotenone | 8.19 | 20.56 |
| Antimycin A | 4.1 | 12.4 |
| Azide | 612.89 | 25.73 |
| CCCP | 46.73 | 12.59 |

With the exception of *S. aureus* treated with azide, the fluorescence values for the treated samples were all lower than the fluorescence values of the untreated samples. These results demonstrate that compound (19) can be used to monitor the vitality of cells treated with various drugs and inhibitors.

Example 28

Electron Transport System Inhibition Using Compound (22)

Stain compound (22) was assayed according to the procedure outlined in Example 23.

TABLE 8

ETS assays with compound (22)

| Inhibitor | S. aureus | E. coli |
|---|---|---|
| Untreated | 594.12 | 90.91 |
| Rotenone | 11.74 | 38.81 |
| Antimycin A | 6.16 | 20.17 |
| Azide | 765.59 | 62.12 |
| CCCP | 240.61 | 63.26 |

With the exception of *S. aureus* treated with azide, the fluorescence values for the treated samples were all lower than the fluorescence values of the untreated samples. These results demonstrate that compound (22) can be used to monitor the vitality of cells treated with various drugs and inhibitors.

Example 29

Electron Transport System Inhibition Using Compound (24)

Stain compound (24) was assayed according to the procedure outlined in Example 23.

TABLE 9

ETS assays with compound (24)

| Inhibitor | S. aureus | E. coli |
|---|---|---|
| Untreated | 853.47 | 114.71 |
| Rotenone | 17.17 | 44.66 |
| Antimycin A | 6.56 | 26.28 |

TABLE 9-continued

| ETS assays with compound (24) | | |
|---|---|---|
| Inhibitor | S. aureus | E. coli |
| Azide | 1272.336 | 79.45 |
| CCCP | 402.19 | 152.7 |

With the exception of *S. aureus* treated with azide, the fluorescence values for the treated samples were all lower than the fluorescence values of the untreated samples. These results demonstrate that compound (24) can be used to monitor the vitality of cells treated with various drugs and inhibitors.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:

1. A chemical compound having the structure:

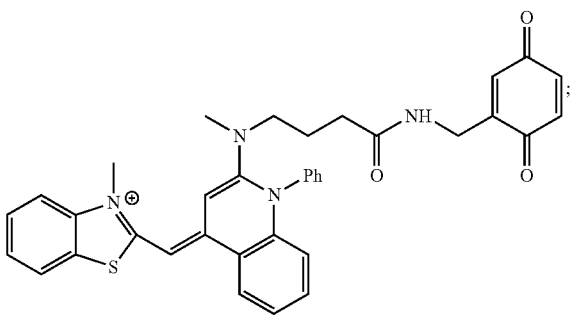
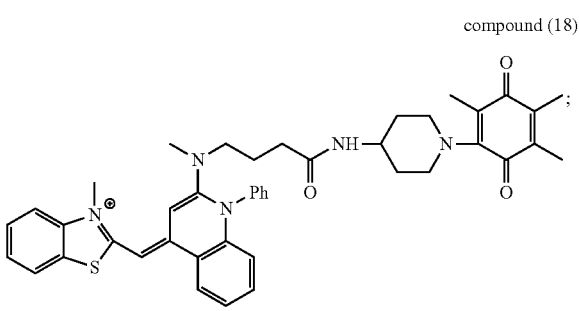 [SMILES: CC1=C(C)C(=O)C(N2CCC(NC(=O)CCCN(C)C3=C/C(=C\c4sc5ccccc5[n+]4C)c4ccccc4N3c3ccccc3)CC2)=C(C)C1=O]
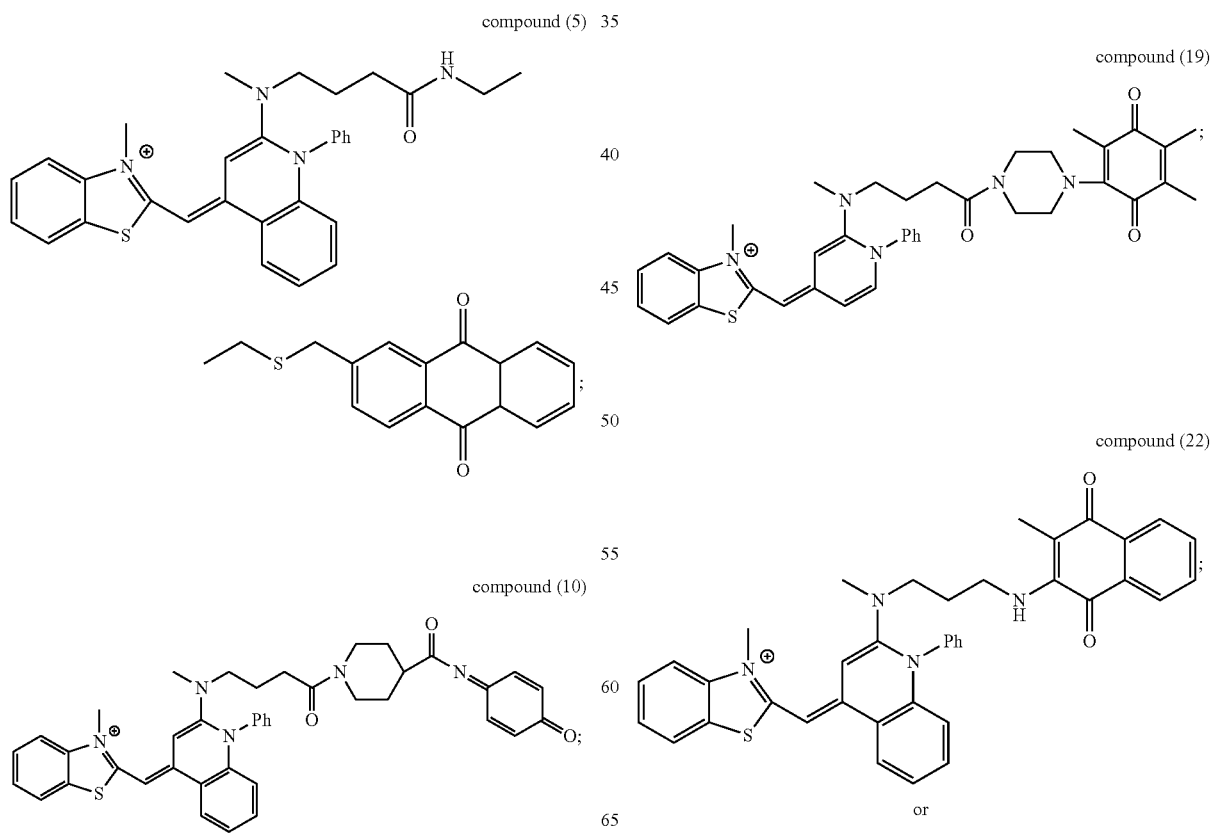

compound (24)
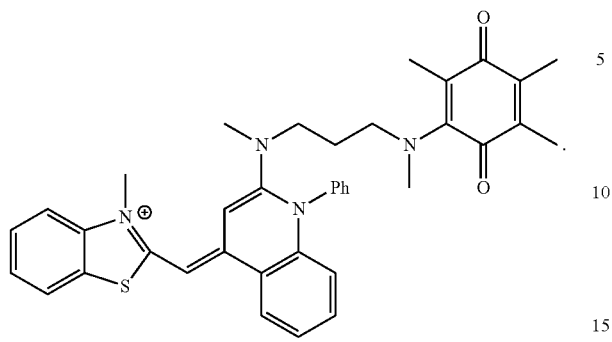
* * * * *